United States Patent [19]
Jacobs

[11] 4,044,762
[45] Aug. 30, 1977

[54] ATHLETIC MOUTHGUARD

[76] Inventor: Alfred G. Jacobs, c/o Safe-T-Gard, Inc., P.O. Box 934, Madison, Wis. 53701

[21] Appl. No.: 716,375

[22] Filed: Aug. 23, 1976

Related U.S. Application Data

[63] Continuation of Ser. No. 331,794, Feb. 12, 1973, abandoned.

[51] Int. Cl.² .............................................. A61M 7/00
[52] U.S. Cl. ................................. 128/136; 128/260; 32/2; 424/151; 264/DIG. 30; 264/16
[58] Field of Search ............... 128/136, 132, 140, 141, 128/142.4, 146.3, 147, 359, 260; 32/2; 424/151, 152; 264/16, 17, 18, DIG. 30

[56] References Cited
U.S. PATENT DOCUMENTS

| | | | |
|---|---|---|---|
| 3,035,003 | 5/1962 | Kessler | 260/28.5 |
| 3,379,193 | 4/1968 | Monaghan | 128/136 |
| 3,527,219 | 9/1970 | Greenberg | 128/136 |
| 3,618,213 | 11/1971 | Shepherd | 32/2 |

*Primary Examiner*—Robert W. Michell
*Assistant Examiner*—Henry J. Recla
*Attorney, Agent, or Firm*—John M. Winter; Theodore J. Long; Harry C. Engstrom

[57] ABSTRACT

An athletic mouthguard for use by participants in contact sports to simultaneously protect and topically treat the teeth. The mouthguard is a generally U-shaped channel molded preferably from a composition of thermoplastic resin and a fluoride compound such as sodium fluoride, stannous fluoride, or sodium fluorosilicate. The fluoride compound is released from the molded resin mouthguard to the wearer's teeth over extended periods of use.

1 Claim, 3 Drawing Figures

ATHLETIC MOUTHGUARD

CROSS REFERENCE TO RELATED APPLICATION

This is a continuation of application Ser. No. 331,794, filed Feb. 12, 1973 now abandoned.

BACKGROUND OF THE INVENTION

This invention relates to the field of athletic mouthguards. Mouthguards molded of a variety of thermoplastic resins which can be quickly and easily custom fit to the teeth by the application of moderate heat and pressure have been known for many years as evidenced by my U.S. Pat. No. 3,312,218. Such mouthguards are presently in wide-spread use by athletes on all levels of sports competition.

Furthermore, the treatment of teeth with topically applied fluoride compounds is also well-known. The topical agent has generally been applied by a dentist or dental assistant who paints the agent on the patient's teeth or by the use of a dental appliance known as a topical arch tray. One type of tray comprises a disposable laminated member having an inner layer of absorbent material to which the topical agent in liquid or gel form is applied just prior to use. The tray is then placed in the patient's mouth about the teeth for the prescribed period of time for the particular treatment. With most topical fluoride treatments this is about 3 to 10 minutes. The tray is then removed and disposed of.

Another form of treatment is to place a fluoride compound gel in a generally U-shaped plastic tray or mouthpiece and place it in the patient's mouth wherein his teeth are impressed into the gel for intimate contact with the teeth over a relatively short prescribed period of time. These treatment procedures have proven particularly useful in the prevention of tooth decay when administered by dentists or their assistants at regularly prescribed intervals.

Other known methods of applying fluoride compounds to the teeth are the use of toothpaste containing fluoride compounds and fluoridated drinking water.

SUMMARY OF THE INVENTION

My invention is a molded thermoplastic resin athletic mouthguard containing a fluoride compound such as sodium fluoride, stannous fluoride, or sodium fluorosilicate which compound is released during use thus providing simultaneous athletic protection for and fluoride treatment of the teeth of the wearer.

While the fluoride compound might be applied to the mouthguard in several ways, preferably it is incorporated into the molding composition itself by mixing it with the thermoplastic resin prior to molding. When made in this way and after the mouthguard has been softened in hot water and conformed to the wearer's teeth in the usual fashion, a significant amount of fluoride compound is released to the wearer's teeth during repeated uses.

The incorporation of the fluoride compound in a reuseable athletic mouthguard at the time of manufacture permits the wearer to obtain periodic topical application of fluoride to his teeth while participating in his regular sports activity and without the application of messy liquids or gels.

Other objects, features and advantages of my invention will be apparent from the following detailed description taken in conjunction with the accompanying drawings, together which disclose exemplary and preferred embodiments of the invention.

DESCRIPTION OF A PREFERRED EMBODIMENT

Figure 1:
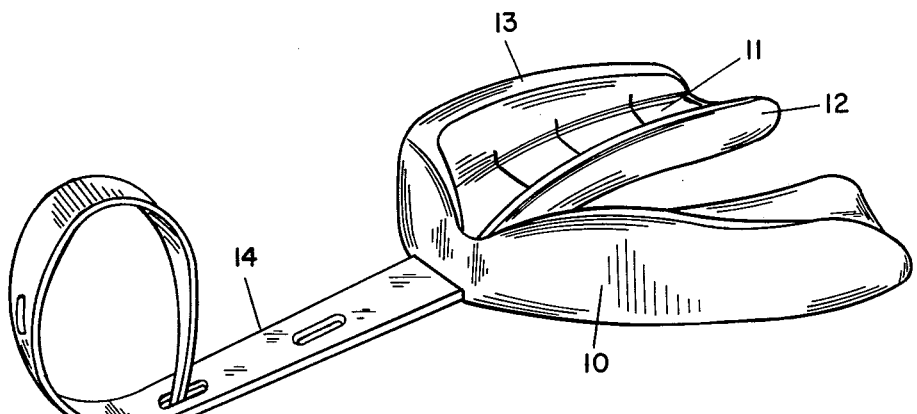
FIG. 1 is an isometric view of an athletic mouthguard embodying my invention with a keeper strap.
Figure 2:
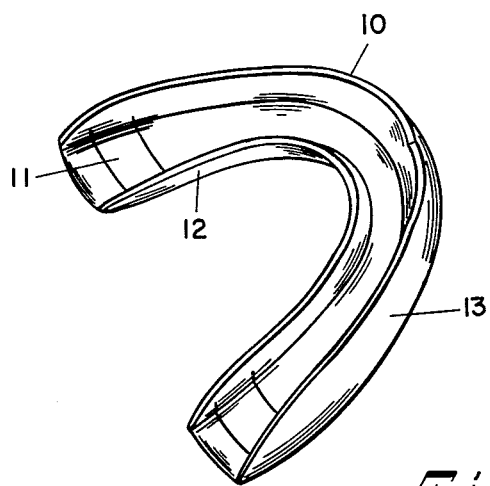
FIG. 2 is an isometric view of another form of mouthguard embodying my invention without a keeper strap.

As shown in the drawings, my mouthguard basically comprises a U-shaped channel member 10 having a base portion 11 connecting an inner wall 12 and an outer wall 13. As shown in FIG. 1, the mouthguard may be formed with an integral keeper strap 14.

The mouthguard shown is made from a composition of a thermoplastic resin and a fluoride compound. The thermoplastic resin material contemplated is such that it can be molded under moderate pressure in the wearer's mouth at a temperature higher than body temperature but lower than that which will burn mouth tissue to permit it to be conformed to the wearer's teeth and surrounding gum tissue and which, after cooling, is tough, resilient, and shape retaining at body temperature. One such preferred material is 505 ethylene vinyl acetate copolymer resin sold by Union Carbide Company. Any suitable thermoplastic resin may be employed, however, other ethylene vinyl acetate copolymer resins which are well-suited for my invention are those sold by the du Pont Company under the names Alathon and Elvax. The mouthguard when made of a suitable thermoplastic resin will become sufficiently softened so as to receive a dental impression under moderate pressure at a temperature between about 120°-150° F., the optimum temperature range for molding the mouthguard in the mouth.

The fluoride compound which in the preferred embodiment forms a portion of the composition from which a mouthguard is molded may be any fluoride containing compound which can beneficially be used to treat the teeth. Examples of such compounds are sodium fluoride (NaF), stannous fluoride ($SnF_2$) and sodium fluorosilicate ($Na_2SiF_6$). The fluoride compound incorporated into the molding composition may range from about 0.5% to about 5% of the total weight of the composition, with about 2% being preferred.

A specific example of a composition which has been successfully used to form a mouthguard embodying the invention is as follows (percent by weight):

| | |
|---|---|
| Union Carbide 505 ethylene vinyl acetate copolymer resin | 98% |
| sodium fluoride (NaF) | 2% |

A suitable mouthguard may be made in accordance with the following ranges (percent by weight):

| | |
|---|---|
| thermoplastic resin<br>example —ethylene vinyl acetate copolymer resin | 99.5-95% |
| fluoride compound<br>examples —sodium fluoride (NaF)<br>stannous fluoride ($SnF_2$)<br>sodium fluorosilicate ($Na_2SiF_6$) | 0.5-5% |

The preferred method of making a mouthguard embodying my invention is to mix about 98 parts by weight of thermoplastic resin beads to two parts by weight of sodium fluoride, stannous fluoride or sodium fluorosilicate powder. The mixture is then heated and mixed until the resin becomes sufficiently molten for molding. The molding temperature of the resin is well below the melting temperature of the powdered fluoride compound constituent of the composition. The composition is then injected into a mold of the desired shape to form the mouthguard.

It is possible to apply the fluoride compound by spraying or otherwise coating a thermoplastic resin mouthguard with the compound and drying, if necessary, prior to packaging.

The mouthguard can be custom fit by the user for intimate contact with the teeth surfaces by heating the mouthguard to a temperature higher than body temperature and sufficient to cause the thermoplastic material to soften and become moldable under moderate pressure. For the preferred materials mentioned herein, the temperature at which the mouthguard may be readily molded in the mouth is approximately 120°-⅛° F. This temperature can generally be achieved by placing the mouthguard in boiling water for about 10 seconds. The mouthguard is then removed from the water and immediately placed in the mouth around the teeth to be protected and treated. The user then sucks substantially all of the air and water out of the mouthpiece to draw the mouthpiece tightly against the teeth and thereby impress the outline of the teeth into the base portion and the inner and outer walls of the mouthpiece. Upon cooling to body temperature, the mouthguard will retain the dental impression.

Figure 3:
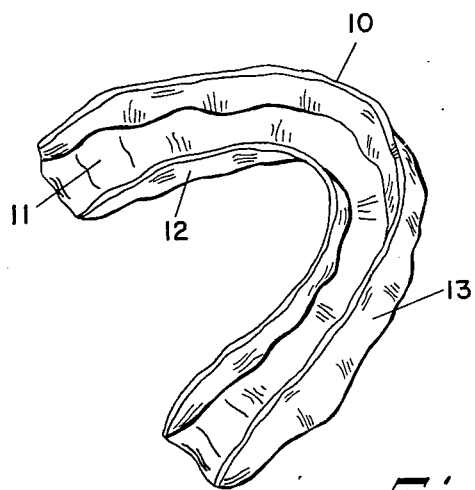
FIG. 3 is an isometric view of the mouthguard shown in FIG. 2 after it has been custom fit by the user.

As shown in FIG. 3, the inner surfaces of the base portion 11, inner wall 12, and outer wall 13 will bear a distinct impression of the wearer's teeth and surrounding gum tissue. This custom fit provides maximum tooth contact for the most effective protection and fluoride treatment.

It is understood that the present invention is not confined to the particular construction, materials, and method herein illustrated and described, but embraces all such modified forms thereof as come within the scope of the following claims.

I claim:

1. A generally U-shaped athletic mouthguard molded from a composition of liquid impermeable ethylene vinyl acetate copolymer and not more than 5% by weight fluoride compound selected from the group consisting essentially of sodium fluoride, stannous fluoride, and sodium fluorosilicate; said liquid impermeable ethylene vinyl acetate copolymer having a melting point below the fluoride compound whereby when heated to a temperature in excess of normal human body temperature can be molded to receive an impression of the wearer's teeth and when cooled to the normal human body temperature is resilient and shape retaining.

* * * * *